United States Patent [19]

Deckwer et al.

[11] Patent Number: 5,338,681
[45] Date of Patent: Aug. 16, 1994

[54] METHOD OF ISOLATING POLYSACCHARIDE PRODUCING BACTERIA FROM NON-POLYSACCHARIDE PRODUCING BACTERIA WITH GELLAN

[75] Inventors: Wolf-Dieter Deckwer; Detlef Lobas; Adrian Schumpe, all of Braunschweig, Fed. Rep. of Germany

[73] Assignee: Gesellschaft fur Biotechnologische Forschung mbH GBF, Braunschweig, Fed. Rep. of Germany

[21] Appl. No.: 858,114

[22] Filed: Mar. 26, 1992

[51] Int. Cl.$^5$ .................. C12P 19/12; C12P 19/04; C12N 1/02; C12N 1/20
[52] U.S. Cl. .................. 435/252.1; 435/100; 435/101; 435/170; 435/252.4; 435/253.6; 435/261; 435/874
[58] Field of Search .............. 435/100, 101, 170, 874, 435/252.1, 252.4, 253.6, 261

[56] References Cited

U.S. PATENT DOCUMENTS

| | | | |
|---|---|---|---|
| 4,535,153 | 8/1985 | Kang et al. | 435/104 |
| 4,567,140 | 1/1986 | Voelskow et al. | 435/101 |
| 5,071,976 | 12/1991 | Stirling | 435/101 |
| 5,093,253 | 8/1992 | Nolan | 435/170 |
| 5,125,099 | 6/1992 | Cornish et al. | 435/252.2 |
| 5,130,249 | 7/1992 | Hardin et al. | 435/252.1 |

Primary Examiner—David M. Naff
Assistant Examiner—Deborah K. Ware
Attorney, Agent, or Firm—Kane, Dalsimer, Sullivan, Kurucz, Levy, Eisele and Richard

[57] ABSTRACT

The invention relates to a method for isolating a polysaccharide extracellularly producing bacteria from a mixed culture of non-polysaccharide and polysaccharide producing bacteria, The method uses a streaking technique on a nutrient medium containing unsubstituted gellan as a gellant. The polysaccharide extracellularly producing bacteria are isolated by the act of non-polysaccharide extracellularly producing bacteria sinking into the nutrient medium. However, the polysaccharide extracellularly producing bacteria do not sink into the nutrient medium. The isolated cells are capable of producing an exopolysaccharide such as P4. Further the isolated cells are capable of producing gellan. The specific polysaccharide producing bacteria are of the genera Auromonas, Pseudomonas and Sphingomonas.

13 Claims, 4 Drawing Sheets

METHOD OF ISOLATING POLYSACCHARIDE PRODUCING BACTERIA FROM NON-POLYSACCHARIDE PRODUCING BACTERIA WITH GELLAN

BACKGROUND OF THE INVENTION

1. Field of the Invention

The invention relates to methods of isolating microorganisms and more particularly to an improved method of isolating polysaccharide producing microorganisms.

2. Brief Description of Related Art

It is desired to improve the prior art relating to the biological production of polysaccharides.

Gellan, for example, is a microbial anionic heteropolysaccharide composed of tetrasaccharide units produced by *Auromonas elodea* ATCC 31461. Native gellan is substituted by acetyl and L-glyceric acid radicals. These substituents can be eliminated readily by treatment with alkali. The resulting unsubstituted gellan (named hereinafter gellan/u) is a product of industrial interest which has the physical property of thermoreversibly forming gels in aqueous solutions. Gellan/u is already marketed as an agar substitute (Gelrite, manufactured by Kelco, Rahway/USA). A wide range of applications is feasible for the food industry. Approval of a food additive has already been applied for in the USA and in Europe; see V. J. Morris, Food Biotechnology 4 (1990) No. 1, p. 45-57. In Japan, gellan was approved as a food additive as early as 1988; see V. J. Morris, supra.

Bacterial species in which the formation of a polysaccharide such as, for example, gellan, has been observed, are known. The difficulty arising from the use of such species for the production of polysaccharides is that not all strains, clones or cells of this species produce the desired polysaccharide efficiently and extracellularly.

Surprisingly, it has now been found that cells which produce gellan extracellularly do not sink into a gellan matrix, while cells which do not produce gellan extracellularly submerge in the gellan matrix. Starting from the abovementioned observation, a method has now been developed by means of which cells and clones can be isolated which produce a desired polysaccharide, such as gellan, efficiently and extracellularly.

SUMMARY OF THE INVENTION

To achieve the object on which the invention is based, a method is proposed, according to an embodiment of the invention, for isolating cells of a bacterial species in which the production of a polysaccharide is observed, the cells to be isolated producing the polysaccharide extracellularly, and the method being characterised in that (a) a nutrient medium is used which contains unsubstituted gellan as the gellant,
(b) cells of the starting species are separated by the streak method, and
(c) cells or clones, which do not sink into the nutrient medium matrix, are isolated.

DETAILED DESCRIPTION OF THE PREFERRED EMBODIMENTS OF THE INVENTION

In the method according to the invention, cells of a bacterial species, in which the production of a polysaccharide has been observed, may be used as starting material, and cells or clones may be isolated which produce the polysaccharide extracellularly in a more efficient manner than the starting culture.

It is also possible, in the method according to the invention, to start from cells of a bacterial species in which the production of gellan is observed, and to isolate cells or clones which produce gellan extracellularly.

This can be done by starting from cells of a species from the genus Auromonas or Sphingomonas, in particular cells of the species *Auromonas elodea* or *Sphingomonas paucimobilis*, for example cells of *Auromonas elodea* ATCC 31461. *Sphingomonas paucimobilis* DSM 6314, which is an efficient gellan producer, was obtained from this culture by the method according to the invention.

Furthermore, it is possible to start, in the method according to the invention, from cells of a bacterial species in which the production of polysaccharide P4 is observed, and to isolate cells or clones which produce P4 extracellularly.

First analyses (sugar sequencing) have shown that the exopolysaccharide P4 is composed of two parts of glucose and one part of rhamnose. P4 shows viscosity-increasing properties in aqueous solution. The viscosity of aqueous P4 solutions remains stable in the range of pH 2 to pH 10 and at temperatures of up to approximately 80° C. The viscosity of aqueous P4 solutions decreases only gradually with increasing salinity. After heating in alkaline medium, P4 gives solid gels.

This can be done by starting from cells of a species from the genus Pseudomonas or Sphingomonas, in particular cells of the species *Pseudomonas paucimobilis* or *Sphingomonas paucimobilis*, in particular cells of *Pseudomonas paucimobilis* NCIMB 11 942. *Sphingomonas paucimobilis* DSM 6 418, also termed P4 hereinafter, which is an efficient P4 producer, was obtained from this culture by the method according to the invention.

A further embodiment of the invention provides *Sphingomonas paucimobilis* DSM 6314. This is a strain which has been obtained by the method according to the invention and produces gellan extracellularly and in an efficient manner.

Furthermore, another embodiment of the invention provides *Sphingomonas paucimobilis* DSM 6 418. This is a strain which has been obtained by the method according to the invention and produces P4 extracellularly and in an efficient manner.

Finally, a further embodiment of the invention provides a method for the batchwise or continuous production of a polysaccharide, which is characterised in that the polysaccharide is produced with the aid of cells, or clones of these cells, which have been obtained by the method according to the invention.

Examples of the method according to the invention relate to the production of gellan or P4.

SCIENTIFIC BACKGROUND

A recently developed screening technique allowed two strains to be isolated from a culture of strain (ATCC 31461) *Auromonas elodea*; see R. Moorhouse, Structure/property relationships of a family of microbial polysaccharides, in: Industrial Polysaccharides: Genetic Engineering, Structure/property Relations and Applications. edited M. Yalpani, Vol. 3, Elsevier Science Publishers, Amsterdam 1987, p. 187–205, (before 1987 *Pseudomonas elodea*; see K. S. Kang, G. T. Veeder, P. J. Mirrasoul, T. Kaneko and I. W. Cottrell. Applied and Environmental Microbiology 43 (1982) No. 5, p. 1086–1091), whose characterisation by the Deutsche Sammlung yon Mikroorganismen und Zellkulturen [German Collection of Microorganisms and Cell Cultures] (DSM), Brunswick, gave a classification under the systematic name *Sphingomonas paucimobilis*. These strains are novel microorganisms which were hitherto unknown and which differ from those of strain (ATCC 31461) with regard to several properties. Culture (ATCC 31461) is referred to in the literature as pleomorphic; Kang et al, supra. Kang et al.; Supra., also mention that good growth and good gellan production only result from the use of a freshly plated culture for the inoculum; see U.S. Pat. No. 4,326,052. This may partly be attributed to the fact that non-producing variants predominate as the culture grows older. Amongst the two variants of strain *Sphingomonas paucimobilis* which were isolated as a pure culture, only variant E2, and not variant E1, produces extracellular polysaccharide. Variant *Sphingomonas paucimobilis* E2, which is of interest from the industrial point of view, was deposited at the DSM as a lyophilisate with the number 6314. Mixed cultures of variants E1 and E2 also loose their potential for producing the polysaccharide gellan relatively rapidly. Ignorance of these facts leads to highly heterogeneous results in the fermentations, caused by uncontrollable inoculum.

As a further advantage of the recently developed screening technique, it was possible to isolate a variety of different strains from a culture of strain *Pseudomonas paucimobilis* (NCIMB 11942); see A. Anson, P. J. Fisher, A. F. D. Kennedy and I. W. Sutherland, Journal of Applied Bacteriology (1987) No. 62, p. 147–150. Characterisation, by the Deutsche Sammlung von Mikroorganismen und Zellkulturen [German Collection of Microorganisms and Cell Cultures] (DSM), Brunswick, of variant P4 which has been obtained as a pure culture also gave a classification under the systematic name *Sphingomonas paucimobilis*. This variant is a novel microorganism species which was hitherto unknown and which differs from strain *Pseudomonas paucimobilis* (NCIMB 11942) with regard to a variety of properties. From amongst the variants which have been isolated from culture *Pseudomonas paucimobilis* (NCIMB 11942), only variant *Sphingomonas paucimobilis* P4 produces extracellular polysaccharide P4. Variant *Sphingomonas paucimobilis* P4, which is of interest from an industrial point of view, was deposited at the DSM as a lyophilisate with the number 6418. Mixed cultures of the variants lose their potential for producing polysaccharide P4 relatively rapidly.

When fermented aerobically, *Sphingomonas paucimobilis* E2 (DSM 6314) produces the exopolysaccharide gellan from a variety of carbon sources such as, for example, glucose, with ammonium nitrate or other nitrogen sources in the presence of mineral salts and trace elements and with or without complex nutrient media. The fermentation time for the conversion of 30 kg/m$^3$ glucose is less than 46.5 hours. The behaviour of the fermentation liquor is thixotropic. After shearing, the flow properties of the pseudoplastic gellan solutions can be described by the Ostwald - de Waele relationship. The viscosity increases considerably during fermentation. At the end of the fermentation, consistency factors of above 20,000 mPa s$^n$ are reached. The flow index n drops to a value of 0.11. The pure gellan yield is above 28% relative to the carbon source employed. This means a considerable increase in product yield compared with the conventional method. Kang et al. [3] obtain 50% by weight of polysaccharide and biomass relative to the carbon source employed, of which approximately 50% by weight is composed of protein and insoluble (cellular) components, i.e. the pure gellan yield according to these data is 25% by weight relative to the carbon source employed; see U.S. Pat. Nos. 4,326,052 and 4,326,053 to Kang et al. Since deviations due to different analytical methods are possible, tests were carried out by the applicant using strain *Auromonas elodea* (ATCC 31461). In these comparative fermentations, it was observed that the actual yield of pure, protein-free gellan by Kang's fermentation method using *Auromonas elodea* (ATCC 31461) is considerably lower and in an order of approximately 6–10%.

ISOLATION OF THE CULTURES

When a culture of *Auromonas elodea* (ATCC 31461) or *Pseudomonas paucimobilis* (NCIMB 11942) is plated on solid nutrient media using gellan/u instead of agar, it can be seen after incubation for approx. 48 hours at 30° C. that the colonies sink into the matrix. Experiments without carbon source show no growth, which suggests that gellan/u is not utilised as substrate. However, the microorganisms liquefy the gel. Dilution series of *Auromonas elodea* (ATCC 31461) or *Pseudomonas paucimobilis* (NCIMB 11942) in physiological sodium chloride solution followed by plating on yeast/malt-gellan/u plates demonstrated that a few colonies did not sink into the gellan/u matrix. These cultures proved to be particularly suitable for polysaccharide production. Repeated inoculation and performance of this purification step gave us the pure cultures of strains *Sphingomonas paucimobilis* E2 (DSM 6314) and *Sphingomonas paucimobilis* P4 (DSM 6418). The non-producing variants were obtained by isolation from sinking colonies.

To achieve as high a product yield as possible in the fermentation, contamination by the non-producing variants must be excluded. The best results are achieved by inoculating the first preculture for the fermentation from a dilution series.

MAINTENANCE AND CULTURE TECHNIQUE

Routine maintenance of *Sphingomonas paucimobilis* E2 (DSM 6314) can be effected on yeast/malt plates, using agar or gellan/u as the gellant, on which good growth can be observed. Routine maintenance of *Sphingomonas paucimobilis* P4 (DSM 6418) can be effected on Czapek Dox plates or on yeast/malt plates: both media show good growth. The producing strain variants are selected on yeast/malt-gellan/u plates. The plates are generally incubated for 1–2 days at 30° C.

The cultures can be stored for approx. 1–2 weeks at 4° C. without the microorganisms losing their activity. A different type of preservation is, for example, deep-freezing of the cultures at −20° C. without pretreatment. However, an intermediate plating of these cultures should be carried out before they are used. The cultures were deposited at the DSM in the form of lyophilisates.

Flasks containing 25 ml of the fermentation medium were used for the first preculture. Every following step was inoculated with in each case 10% of its volume of inoculum from the previous step. Incubation was effected in each case for 24 hours at 30° C. on a shaker at 180 rpm.

All components of the nutrient medium with the exception of glucose were sterilised together at 121° C. Glucose was dissolved separately and sterilised to avoid caramelisation. The glucose solution and the solution with the other components were combined in a clean bench to give the nutrient solution. Kang's nutrient medium (Kang et al., supra) which is used for the submerged cultures (shaking flasks and fermenters) has the following composition:

3.3% of glucose $H_2O$
0.01% of $MgSO_4 \cdot 7H_2O$
0.09% of $NH_4NO_3$
0.05% of Promosoy (Central Soya Overseas B.V., Chem. Div., Rotterdam)
1 ml of Concentrated trace element solution
5 ml of Potassium phosphate buffer pH 7 (1 molar)

The concentrated trace element solution has the following composition:

| | |
|---|---|
| Manganese chloride $4H_2O$ | 1.800 g/l |
| Iron(II) sulphate $7H_2O$ | 2.488 g/l |
| Boric acid | 0.285 g/l |
| Copper sulphate $5H_2O$ | 0.052 g/l |
| Zinc chloride | 0.021 g/l |
| Cobalt chloride $6H_2O$ | 0.074 g/l |
| Magnesium molybdate | 0.023 g/l |
| Sodium nitrate $2H_2O$ | 2.1 g/l |

Media compositions other than the one listed were also successfully used for gellan production and for the production of polysaccharide P4.

Characterisation of Strain *Sphingomonas paucimobilis* E2 (DSM 6314)

Morphology

The bacteria *Sphingomonas paucimobilis* E2 (a subculture of this microorganism is available from Deutsche Sammlung von Mikroorganismen and Zellbulturen, Mascheroder Weg 1B, D-3300 braunschweeiz, Germany under accession number DSM 6314) are Gram-negative rod-shaped cells of a width of 0.6–0.8 μm and a length of 1.5–4.0 μm. In fresh cultures, the cells show a high degree of motility. With increasing age of the cultures, the motility is largely restricted due to the polysaccharide formed. The microorganisms only grow aerobically.

After 48 hours' incubation on Y/M agar, the bacteria form colonies of a diameter of 2–3 mm. The colonies have a yellow colour due to a non-diffusible pigment. Strain variant E1 is intense yellow and produces hard, non-viscous colonies on solid nutrient media. Variant E2 shows a slightly darker yellow on solid nutrient media than variant E1. Due to the polysaccharide formed, colonies of variant E2 are viscous. E2 plates which have been incubated over a prolonged period show transparent colonies which include yellow cell clumps, suggesting that considerable amounts of polysaccharide are excreted.

Physiology and Biochemical Properties

The Deutsche Sammlung von Mikroorganismen und Zellkulturen [German Collection of Microorganisms and Cell Cultures] (DSM), Brunswick, was commissioned by us to characterise the cultures biochemically. These investigations revealed that *Sphingomonas paucimobilis* E2 (DSM 6314) was a novel species which was hitherto unknown. *Auromonas elodea* (ATCC 31461) showed considerable differences in a parallel test. The bacterial culture *Sphingomonas paucimobilis* E2 (DSM 6314) has the following physiological and biochemical properties:

TABLE 1

| Characterisation of *Sphingomonas paucimobilis* E2 (DSM 6314) | |
|---|---|
| Test/property | |
| Lysis by 3% KOH | + |
| Aminopeptidase (Cerny) | + |
| Spores | − |
| Oxidase | + |
| Catalase | + |
| Growth | − |
| anaerobic | |
| 37/40° C. | ± |
| pH 5.6 | − |
| MacConkey agar | − |
| SS agar | − |
| Cetrimide agar | − |
| Pigments | yellow |
| Non-diffusible | + |
| Diffusible | − |
| Fluorescent | − |
| pyocyanin | − |
| Acid from (OF test) | |
| Glucose, aerobic | − |
| Glucose, anaerobic | − |
| Gas from glucose | − |
| Acid from (ASS) | |
| Glucose | + |
| Fructose | + |
| Xylose | + |
| Arabinose | + |
| Fucose | − |
| Maltose | + |
| Mannose | + |
| Lactose | + |
| Sucrose | + |
| Trehalose | + |
| Cellobiose | + |
| Rhamnose | − |
| Raffinose | + |
| Melezitose | + |
| Melibiose | + |
| Aldonitol | − |
| Dulcitol | − |
| Inositol | − |
| Mannitol | − |
| Sorbitol | − |
| N-Acetylglucosamine | + |
| Glycerol | − |
| ADH | − |
| ODC | − |
| VP | − |

TABLE 1-continued

| Characterisation of *Sphingomonas paucimobilis* E2 (DSM 6314) | |
|---|---|
| Test/property | |
| Indole | − |
| NO$_2$ from NO$_3$ | − |
| Denitrification | − |
| Phenylalanin deaminase | − |
| Levan from sucrose | − |
| Lecithinase | − |
| Urease | − |
| Hydrolysis of | |
| Starch | + |
| Gelatine | − |
| Casein | − |
| DNA | + |
| Tween 80 | + |
| Aesculin | + |
| Tyrosine degradation | + |
| Utilisation of substrates | |
| Acetate | + |
| Adipate | − |
| Caprate | − |
| Citrate | − |
| Glycolate | ± |
| Lactate | − |
| Laevulinate | − |
| Malate | + |
| Malonate | − |
| Phenylacetate | − |
| Suberate | − |
| L-arabinose | + |
| Fructose | + |
| Glucose | + |
| Mannose | + |
| Xylose | + |
| Mannitol | − |
| Gluconate | − |
| 2-ketogluconate | − |
| N-acetylglucosamine | + |
| L-histidine | − |
| L-serine | − |
| Hydroxybutyrate | − |

Characterisation of Strain *Sphingomonas paucimobilis* P4 (DSM 6418)

Morphology

The bacteria *Sphingomonas paucimobilis* P4 (a subculture of this microorganism is available from the Deutsche Sammlung von Miikroorganismen and Zellkulturen, Mascheroder Wey 1B, D-3300 Braunschweig, Germany under accession number DSM 6418) are Gram-negative rod-shaped cells of a width of 0.6-0.8 μm and a length of 1.5-4.0 μm. In fresh cultures, the cells show a high degree of motility. With increasing age of the cultures, the motility is largely restricted due to the polysaccharide formed. The microorganisms only grow aerobically.

After 48 hours' incubation on Y/M agar, the bacteria form colonies of a diameter of 1-2 mm. The colonies have a yellow colour due to a non-diffusible pigment. Strain variant P4 is intense yellow and produces hard, non-viscous colonies on solid nutrient media. On Czapek Dox agar, the colonies appear bright yellow and slightly transparent; the colonies on this medium are extremely hard and tough.

Physiology and Biochemical Properties

The Deutsche Sammlung von Mikroorganismen und Zellkulturen [German Collection of Microorganisms and Cell Cultures] (DSM), Brunswick, was commissioned by us to characterise the cultures biochemically.

These investigations revealed that *Sphingomonas paucimobilis* P4 (DSM 6418) was a novel species which was hitherto unknown. *Pseudomonas paucimobilis* (NCIMB 11942) showed considerable differences in a parallel test. The bacterial culture *Sphingomonas paucimobilis* P4 (DSM 6418) has the following physiological and biochemical properties:

TABLE 2

| Characterisation of *Sphingomonas paucimobilis* P4 (DSM 6418) | |
|---|---|
| Test/property | |
| Lysis by 3% KOH | + |
| Aminopeptidase (Cerny) | + |
| Spores | − |
| Oxidase | + |
| Catalase | + |
| Growth anaerobic | − |
| 37/40° C. | ± |
| pH 5.6 | − |
| MacConkey agar | − |
| SS agar | − |
| Cetrimide agar | − |
| Pigments | yellow |
| Non-diffusible | + |
| Diffusible | − |
| Fluorescent | − |
| pyocyanin | − |
| Acid from (OF test) | |
| Glucose, aerobic | − |
| Glucose, anaerobic | − |
| Gas from glucose | − |
| Acid from (ASS) | |
| Glucose | + |
| Fructose | + |
| Xylose | + |
| Arabinose | + |
| Fucose | − |
| Maltose | + |
| Mannose | + |
| Lactose | + |
| Sucrose | + |
| Trehalose | + |
| Cellobiose | + |
| Rhamnose | − |
| Raffinose | + |
| Melezitose | + |
| Melibiose | + |
| Aldonitol | − |
| Dulcitol | − |
| Inositol | − |
| Mannitol | − |
| Sorbitol | − |
| N-Acetylglucosamine | − |
| Glycerol | − |
| ADH | − |
| ODC | − |
| VP | − |
| Indole | − |
| NO$_2$ from NO$_3$ | − |
| Denitrification | − |
| Phenylalanin deaminase | − |
| Levan from sucrose | − |
| Lecithinase | − |
| Urease | − |
| Hydrolysis of | |
| Starch | + |
| Gelatine | − |
| Casein | − |
| DNA | + |
| Tween 80 | + |
| Aesculin | + |
| Tyrosine degradation | + |
| Utilisation of substrates | |
| Acetate | + |
| Adipate | − |
| Caprate | − |
| Citrate | − |
| Glycolate | − |

TABLE 2-continued

Characterisation of *Sphingomonas paucimobilis* P4 (DSM 6418)

| Test/property | |
|---|---|
| Lactate | − |
| Laevulinate | − |
| Malate | + |
| Malonate | − |
| Phenylacetate | − |
| Suberate | − |
| L-arabinose | + |
| Fructose | + |
| Glucose | + |
| Mannose | + |
| Xylose | + |
| Mannitol | − |
| Gluconate | − |
| 2-ketogluconate | − |
| N-acetylglucosamine | + |
| L-histidine | − |
| L-serine | + |
| Hydroxybutyrate | − |

Comparison of *Sphingomonas paucimobilis* E2 and P4 with *Auromonas elodea* (ATCC 31461) and *Pseudomonas paucimobilis* (NCIMB 11942)

Strains *Sphingomonas paucimobilis* E2 and P4 differ from the starting cultures *Auromonas elodea* (ATCC 31461) and *Pseudomonas paucimobilis* (NCIMB 11942) in essential properties. The table which follows lists those properties in which differences were found.

Table 3

Comparison of the differences of variants E2 and P4 of *Sphingomonas paucimobilis* and *Auromonas elodea* (ATCC 31461) and *Pseudomonas paucimobilis* (NCIMB 11942)

TABLE 3

Comparison of the differences of variants E2 and P4 of *Sphingomonas paucimobilis* and *Auromonas elodea* (ATCC 31461) and *Pseudomonas paucimobilis* (NCIMB 11942)

| Properties of the strain | DSM 6314 (E2) | ATCC 31461 | DSM 6418 (P4) | NCIMB 11942 |
|---|---|---|---|---|
| Shape of cell: | | | | |
| Length μm | 1.5–4.0 | 1.5–5.0 | 1.5–4.0 | 1.5–4.0 |
| Growth at 37° C.: | + | − | + | + |
| Acid from (ASS): | | | | |
| Fucose | − | − | + | + |
| Melezitose | + | − | + | − |
| N-acetylglucosamine | + | + | − | + |
| Liquefaction of gellan/u gel: | − | + | − | + |
| Utilisation of substrate: | | | | |
| L-arabinose | + | w | + | w |
| 2-ketogluconate | − | + | − | + |
| L-serine | − | − | + | + |

EXAMPLE 1 (COMPARATIVE FERMENTATIONS)

The following text is intended to compare typical batch fermentations of strains *Sphingomonas paucimobilis* E2 (DSM 6314) and *Auromonas elodea* (ATCC 31461). Both fermentations were carried out under identical conditions in a Biostat E fermenter (B. Braun, Melsungen) on a 10 l scale. Four flasks each containing 25 ml of the abovementioned culture medium of a 3-day-old yeast/maltgellan/u plate were inoculated to give the first preculture. The second preculture (four flasks each containing 250 ml) were inoculated after 24 hours with the entire amount of the first preculture. After a further 24 hours, this second preculture was used as inoculum for the fermenter.

The fermenter was aerated with 0.33 vvm of air. The temperature was 30° C. To avoid stagnant zones in the fermenter and to guarantee thorough mixing, the culture solution was stirred with a four-stage Intermig stirrer (diameter 63% of the diameter of the container) at 800 rpm. The culture medium was adjusted to a pH of 7, which was kept constant by means of 1N sodium hydroxide solution and 1N phosphoric acid via a control unit.

Figure 1:
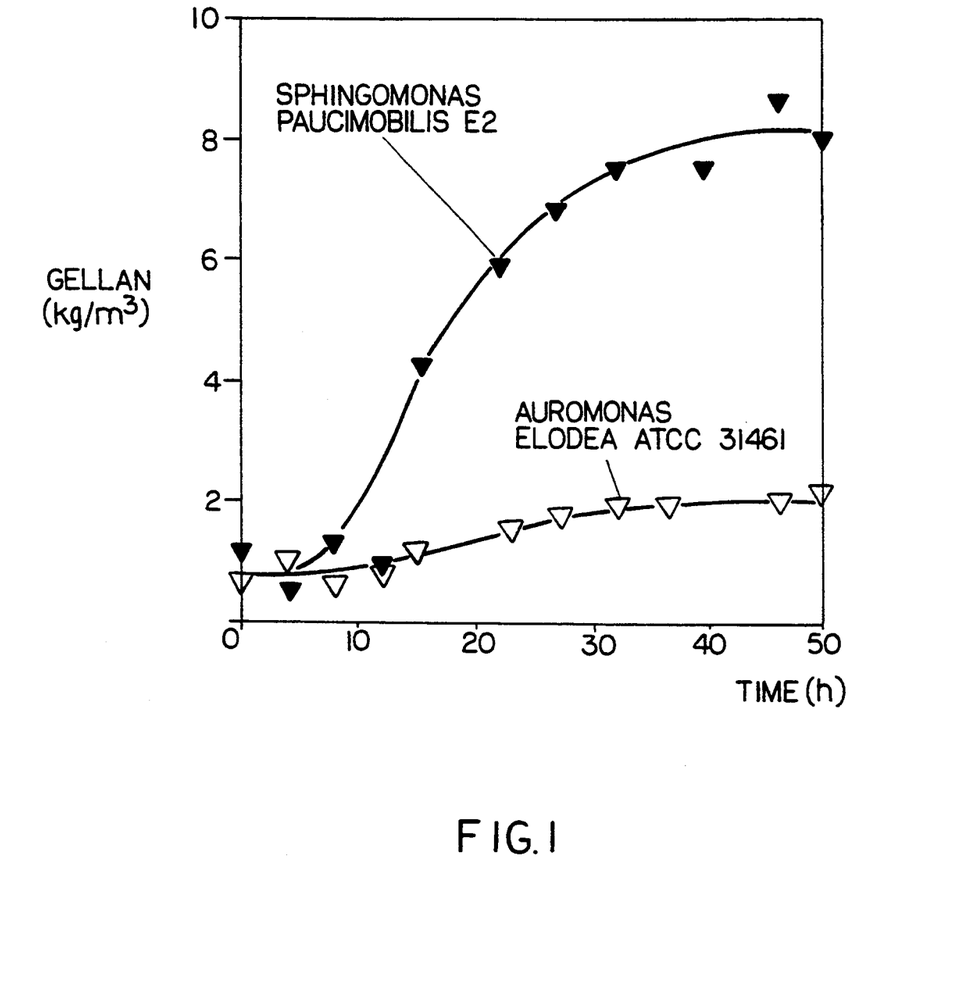
FIG. 1 is a graphical representation of Gellan concentrations as a function of time in fermentations with *Sphingomonas paucimobilis* E2 (DSM 6314) and *Auromonas elodea* (ATCC 31461) following the procedure of Example 1, infra.

At the end of the fermentation, the gellan concentration in the case of *Sphingomonas paucimobilis* E2 (DSM 6314) exceeded that of the fermentation with *Auromonas elodea* (ATCC 31461) approximately by a factor of 4 (FIG. 1). The maximum gellan concentrations were 8 kg/m$^3$ in the case of *Sphingomonas paucimobilis* E2 (DSM 6314) and 2 kg/m$^3$ in the case of *Auromonas elodea* (ATCC 31461). The space-time yields of these fermentations were 17.2 kg/m$^3$ h in the case of *Sphingomonas paucimobilis* E2 (DSM 6314), and 4 kg/m$^3$ h in the case of *Auromonas elodea* (ATCC 31461).

The total gellan content and total biomass were determined by adding two parts by volume of isopropanol, centrifuging the batch and drying the solids (48 hours at 80° C.). To determine the dry biomass content, the samples were diluted with distilled water, the cells were removed by centrifugation, the supernatant was decanted off, the sediment was taken up in water and, following recentrifugation and decanting, the sediment was dried. The gellan concentration was determined by calculating the differences from the results of these analyses.

Figure 2:
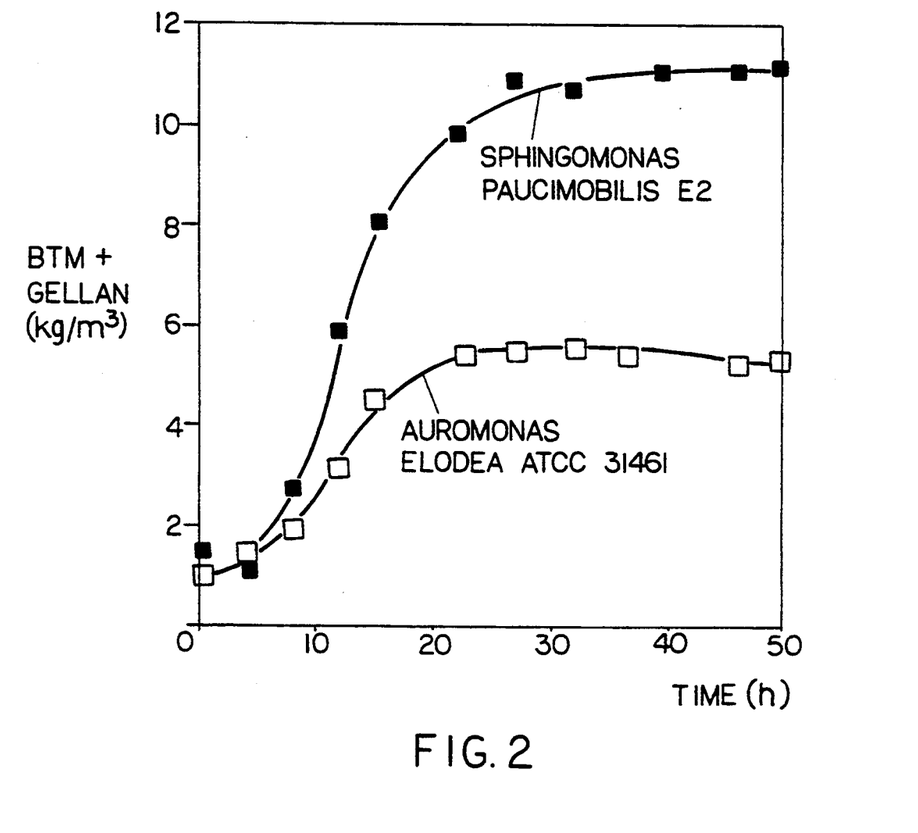
FIG. 2 is a graphical representation of gellan plus biomass as a function of time in fermentations with *Sphingomonas paucimobilis* E2 (DSM 6314) and *Auromonas elodea* (ATCC 31461) following the procedure of Example 1, infra.

The high viscosity of the fermentation liquor in the case of *Sphingomonas paucimobilis* E2 (DSM 6314) required further dilution of the samples prior to centrifugation. This is why the variants of the measured quantities is greater than in the case of the fermentation with *Auromonas elodea* (ATCC 31461). The smallest errors result in the determination of the total of gellan content and biomass content (termed native gellan by Kang, U.S. Pat. No. 4,326,052) from the undiluted fermentation liquor (FIG. 2).

Figure 3:
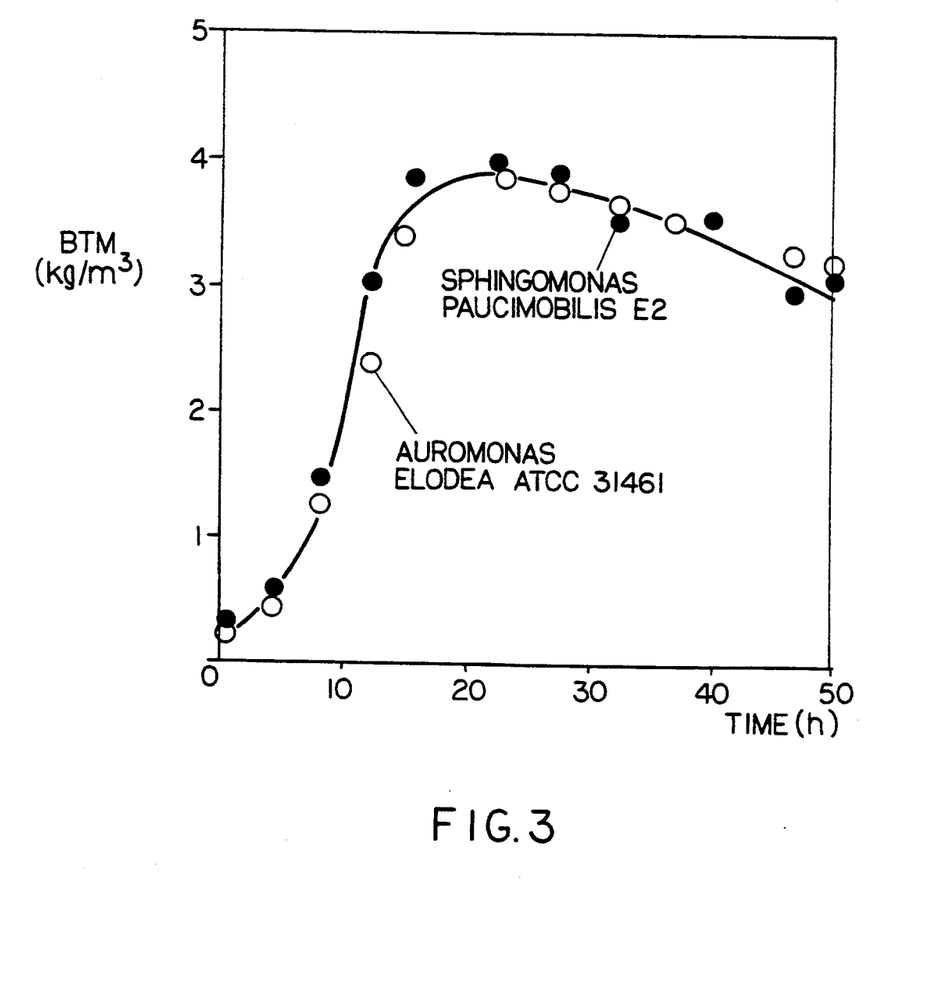
FIG. 3 is a graphical representation of the biomass contents as a function of time in fermentations with *Sphingomonas paucimobilis* E2 (DSM 6314) and *Auromonas elodea* (ATCC 31461) following the procedure of Example 1, infra.

Approximately the same dry biomass contents (DBM) resulted from the two fermentations. The biomass content reached maximum values of approximately 4 kg/m$^3$ at the end of the growth phase. After this, a proportion of the microorganisms died: the biomass content dropped (FIG. 3). In the fermentation with *Sphingomonas paucimobilis* E2 (DSM 6314), the glucose was consumed completely after 46.5 hours, indicating the end of the fermentation. In the case of *Auromonas elodea* (ATCC 31461), 2.3 kg/m$^3$ of glucose remained after 46.5 hours, and 0.42 kg/m$^3$ after 50 hours.

EXAMPLE 2

The fermentation of strain *Sphingomonas paucimobilis* P4 (DSM 6418) proceeded in an essentially similar manner to the above-described fermentations. The fermentation was carried out under the same conditions in a Biostat E fermenter (B. Braun, Melsungen) on a 10 l scale. Four flasks each containing 25 ml of the abovementioned culture medium of a 3-day-old Capek Dox gellan/u plate were inoculated to give the first preculture. The second preculture (four flasks each containing 250 ml) were inoculated after 24 hours with the entire amount of the first preculture. After a further 24 hours, this second preculture was used as inoculum for the fermenter.

The fermenter was aerated with 0.33 vvm of air. The temperature was 30° C. To avoid stagnant zones in the fermenter and to guarantee thorough mixing, the culture solution was stirred with a four-stage Intermig stirrer (diameter 63% of the diameter of the container) at 800 rpm. The culture medium was adjusted to a pH of 7, which was kept constant by means of 1N sodium hydroxide solution and 1N phosphoric acid via a control unit.

Figure 4:
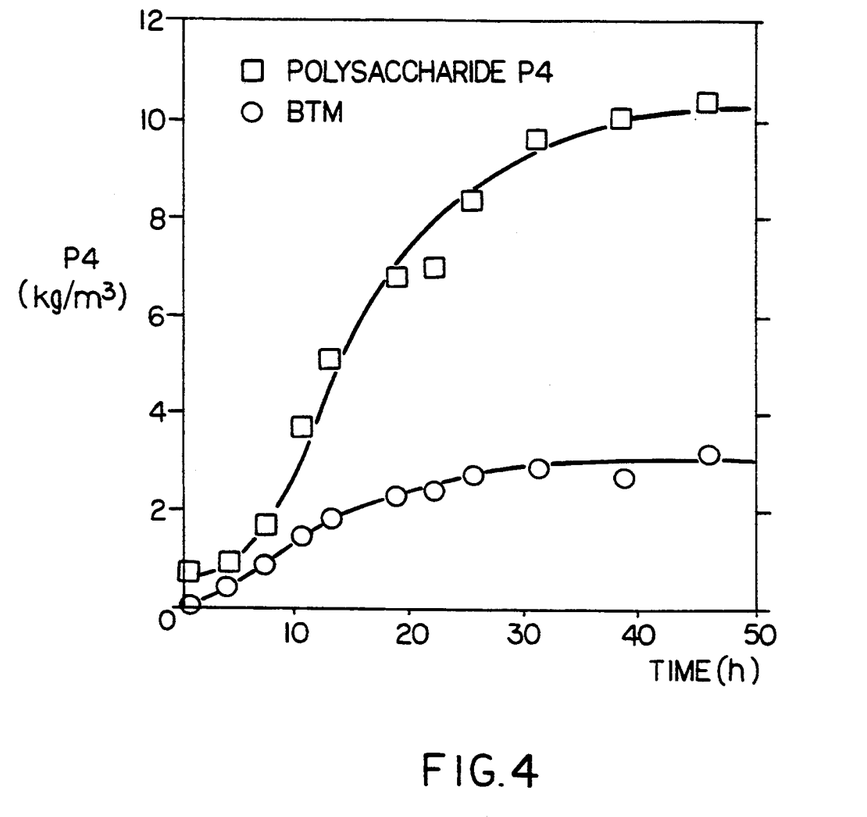
FIG. 4 is a graphical representation of polysaccharide P4 and biomass content as a function of time in fermentation with *Sphingomonas paucimobilis* P4 (DSM 6418) following the procedure of Example 2, infra.

The total P4 content and total biomass were determined by adding two parts by volume of isopropanol, centrifuging and decanting the batch and drying the solids (48 hours at 80° C.). To determine the dry biomass content, the samples were diluted with dimethyl sulphoxide, the cells were removed by centrifugation, the supernatant was decanted off, the sediment was taken up in water and, following recentrifugation and decanting, the sediment was dried. The polysaccharide concentration was determined by calculating the differences from the results of these analyses. The P4 concentration at the end of the fermentation was approx. 10 $kg/m^3$ (FIG. 4).

EXAMPLE 3

The following strains were used:
Leuconostoc mesenteroides DSM 20187
Enterobacter sakazakii DSM 4485
Xanthomonas campestris NRRL B-1459 S4L-II
Aureobasidium pullulans DSM 2404

The media used were the standard media which can be seen in the DSM catalogue "Catalogue of Strains 1989", 4th edition, which were recommended by the DSM to suit the growth requirements of the strains. However, as a modification of the DSM catalogue and in agreement with the method according to the invention, gellan/u was used in all media instead of agar. Streaking of the serial dilutions, incubation and further treatment were carried out in the manner which has been described for the gellan- and P4-producing species in the method according to the invention.

TABLE 4

| Strain | Media used Medium | DSM Catalogue of Strains 1989 |
|---|---|---|
| Leuconostoc mesenteroides (DSM 20187) | MRS | Medium 11, p. 279 |
| Enterobacter sakazakii (DSM 4485) | Nutrient | Medium 1, p. 279 |
| Xanthomonas campestris (NRRL B-1459 S4L-II) | Yeast/malt | See maintenance and culture technique |
| Aureobasidium pullulans (DSM 2404) | Potato Glucose | Medium 129, p. 290 |

Within the cell populations used, strains Enterobacter sakazakii DSM 4485, Xanthomonas campestris NRRL B-1459 S4L-II, Leuconostoc mesenteroides DSM 20187 and Aureobasidium pullulans DSM 2404 showed no sinking cells, on the contrary all cells grew on the surface of the gellan/u plates. It can be concluded from this that the populations employed are pure cultures having a high potential for polysaccharide production.

We claim:

1. Method for isolating a polysaccharide extracellularly producing bacteria from a culture containing a mixture of non-polysaccharide extracellularly producing bacteria, and polysaccharide extracellularly producing bacteria, which comprises;
   (a) streaking a mixture of polysaccharide extracellularly producing bacterial cells and non-polysaccharide extracellularly producing bacterial cells on a nutrient medium which contains unsubstituted gellan as a gellant, and which is effective for growth of the polysaccharide extracellularly producing bacterial cells; and
   (b) culturing the cells on the nutrient medium;
   (c) whereby cells of the polysaccharide extracellularly producing bacteria are isolated from the non-polysaccharide extracellularly producing bacteria cells by not sinking into the nutrient mediums, whereas the non-polysaccharide extracellularly producing cells sink into the nutrient medium.

2. The method according to claim 1, wherein the isolated cells belong to a bacterial species which produce gellan.

3. The method according to claim 1, wherein the isolated cells produce the exopolysaccharide, P4.

4. The method according to claim 2 wherein the polysaccharide producing bacteria is selected from the group consisting of Auromonas and Sphingomonas.

5. The method according to claim 4 wherein the bacteria is Auromonas elodea.

6. The method according to claim 4 wherein the bacteria is Sphingomonas paucimobilis.

7. The method according to claim 4 wherein the bacteria is Auromonas elodea ATCC 31461.

8. The method according to claim 3 wherein the polysaccharide producing bacteria is selected from the group consisting of Pseudomonas and Sphingomonas.

9. The method according to claim 8 wherein the bacteria is Pseudomonas paucimobilis.

10. The method according to claim 8 wherein the bacteria is Sphingomonas paucimobilis.

11. The method according to claim 8 wherein the bacteria is Pseudomonas paucimobilis NCIMB 11 942.

12. Biologically pure Sphingomonas paucimobilis DSM 6 314 cultures free of non-polysaccharide extracellularly producing bacterial cells; and capable of producing polysaccharides extracellularly.

13. Biologically pure Sphingomonas paucimobilis DSM 6 418 cultures free of non-polysaccharide extracellularly producing bacterial cells; and capable of producing polysaccharides extracellularly.

* * * * *